United States Patent [19]

Schlossman et al.

[11] Patent Number: 5,019,648

[45] Date of Patent: May 28, 1991

[54] MONOCLONAL ANTIBODY SPECIFIC FOR THE ADHESION FUNCTION DOMAIN OF A PHAGOCYTE CELL SURFACE PROTEIN

[75] Inventors: Stuart F. Schlossman, Newton Centre; James D. Griffin, Sherborn, both of Mass.

[73] Assignee: Dana-Farber Cancer Institute, Boston, Mass.

[21] Appl. No.: 165,024

[22] Filed: Mar. 7, 1988

Related U.S. Application Data

[63] Continuation-in-part of Ser. No. 70,257, Jul. 6, 1987, abandoned.

[51] Int. Cl.$^5$ ............................................. A01K 39/395
[52] U.S. Cl. ..................................... 530/387; 530/388; 530/380; 530/828; 435/240.27; 435/69.1; 435/70.21; 435/172.2; 424/85.8
[58] Field of Search ............. 435/240.27, 68, 7, 172.2; 530/387, 809; 436/548; 935/100, 104, 107, 110; 424/85.8

[56] References Cited

U.S. PATENT DOCUMENTS 4,840,793  6/1989  Todd, III et al. .................. 424/85.8

OTHER PUBLICATIONS

Dana, N. et al., (I), "Two Functional Domains in the Phagocyte Membrane Glycoprotein Mo1 Identified with Monoclonal Antibodies", *J. Immunol.* 137:3259–3263, Nov. 15, 1986.

Dana, N. et al., (II) "Dysfunctional Mo1 Glycoprotein is Present on a Subline of the KG1 Myelogenous Leukemia Cell Line", *J. Immunol.* 138(10):3549–3554, May 10, 1987.

Letvin, N. L. "Conservation of Myeloid Surface Antigens on Primate Granulocytes," *Blood* 61(2):408–410, 1983.

M. A. Arnaout et al., Deficiency of Two Human Leukocyte Surface Membrane Glycoproteins Mo1 and LFA-2, Fed. Proc 44(10): 2664–2670 (Jul., 1985).

R. F. Todd III et al., Subcellular Localization of the Large Subunit of Mo1 (Mo1α, A Surface Glycoprotein Associated with Neutrophil Adhesion, J. Clin. Invest. 74:1280–1290 (1984).

A. A. TeVelde et al., Antibodies to LFA-1 and Related Molecules Inhibit Conjugate Formation Between Human Peripheral Blood Monocytes and Melanoma Cells, Chem Abstracts 104:500 (No. 184712d) (1986).

*Primary Examiner*—Esther L. Kepplinger
*Assistant Examiner*—Jeff Kushan
*Attorney, Agent, or Firm*—Myron C. Cass

[57] ABSTRACT

A hybrid cell line is developed which produces a monoclonal antibody which binds to a unique antigenic site expressed on the surface of phagocytic cells. The monoclonal antibody binds to and activates a specific domain of the CD11b glycoprotein so as to inhibit adhesion dependent functions of the phagocytic cell, but it does not affect other phagocytic functions. This monoclonal antibody can be used as a reactant in an in vitro diagnostic immunoassay for detecting the unique antigenic site on the surface of normal human neutrophils.

9 Claims, No Drawings

MONOCLONAL ANTIBODY SPECIFIC FOR THE ADHESION FUNCTION DOMAIN OF A PHAGOCYTE CELL SURFACE PROTEIN

This invention was made with funded support of the U.S. Government under PHS Grant No. CA 36167.

RELATED APPLICATION

This application is a continuation-in-part of U.S. Ser. No. 070,257, filed July 6, 1987 and entitled MONOCLONAL ANTIBODY SPECIFIC FOR THE ADHESION FUNCTION DOMAIN OF A PHAGOCYTE CELL SURFACE PROTEIN, now abandoned and is related to the pending application, Ser. No. 061,336, filed June 11, 1987, entitled METHOD OF REDUCING TISSUE DAMAGE AT AN INFLAMMATORY SITE USING A MONOCLONAL ANTIBODY now U.S. Pat. No. 4,840,793. The applicants of this application also are co-applicants named in said related application.

This invention relates to a hybridoma cell line producing a monoclonal antibody which binds to a specific antigenic site expressed on the surface of phagocytic cells. More particularly, this monoclonal antibody binds to and inactivates a specific domain of the CD11b glycoprotein whereby to inhibit adhesion-dependent functions of the phagocytic cell, albeit without affecting the other phagocyte functions.

BACKGROUND OF THE INVENTION

Peripheral blood in the circulatory system of a human is comprised principally of red blood cells, platelets, and white blood cells or leukocytes. The family of white blood cells is comprised of lymphocytes, neutrophils, monocytes, eosinophils, and basophils. Lymphocytes are of T cell or B cell subtypes primarily; additional subsets of lymphocytes are known also. The variety of functions of leukocytes and their clinical relevance has generated great interest in the scientific community.

Neutrophils, eosinophils, and basophils are identified as "granulocytes" because of their content of cytoplasmic granules. Granulocytes and monocytes are identified as "phagocytes" because of their ability to phagocytose or ingest bacteria, other micro-organisms and other types of foreign materials referred to generally as "antigens". This phagocytic function is important in defending the host against a variety of infections and further, is important in various types of inflammatory disorders. Phagocytes are produced from common progenitor cells in the bone marrow circulate in the peripheral blood and finally, enter tissues as necessary for control of infection or for participating in an inflammatory reaction. Such response functions are found in human, and animal phagocytes, i.e., in primates and canines.

The neutrophil is the most common leukocyte in human and animal peripheral blood. One microliter of normal human whole blood includes, on average, $5 \times 10^3$ leukocytes, of which 3,975 are neutrophils, 150 are eosinophils, 25 are basophils, 250 are monocytes, and 1,500 are lymphocytes.

In the immunological response of granulocytes or monocytes to any type of infection or inflammation, these cells are first activated to migrate to the appropriate area in response to "chemo-attractant factors" such as certain bacterial products, complement components, etc. This attraction process is termed "chemotaxis".

Once in an area of inflammation or infection, granulocytes and monocytes then undertake to establish a firm attachment to their targets. For this purpose, these cells possess a number of specific cell surface receptor glycoproteins that promote this interaction, such as complement, Fc, and fibronectin receptors.

One of the most important family of cell surface receptor glycoproteins involved in phagocyte adhesion is the leukocyte cell adhesion molecule family identified as LEU-CAM or CD11/CD18. This family is comprised of at least three (3) cell surface proteins which have two (2) subunits each. They share a common beta subunit, CD18, of 94,000 daltons molecular weight and have different alpha subunits. The known members of this family are termed LFA-1 (CD11a/CD18), Mol (CD11b/CD18), and P150,94 (CD11c/CD18). These glycoproteins have alpha subunits of 180,000, 155,000 and 150,000 dalton molecular weight, respectively. Each of these cell surface proteins have been specifically identified through the use of monoclonal antibodies. The biological importance of this family of surface glycoproteins has been recognized through the identification of a human disease in which leukocytes are genetically deficient in this family of antigens. The disease is characterized by recurrent severe bacterial infections and deficiencies in adhesion-dependent functions, such as, phagocytosis, chemotaxis, leukoaggregation, and neutrophil spreading on plastic.

Mol is a cell surface glycoprotein present on granulocytes, mononuclear phagocytes and null cells (Todd, R.F. III, Nadler, L.M., and Schlossman, S.F., Antigens on human monocytes, *Journal of Immunology.* 126:1435–1442, 1981). In humans, this molecule consists of two non-covalently linked proteins of 155,000 and 94,000 daltons (Todd, R.F. III, van Agthoven, A., Schlossman, S.F., and Terhorst, D., Structure analysis of differentiation antigens Mol and Mo2 on human monocytes, *Hybridoma* 1:329–337, 1982). This complex has been shown to mediate cell adhesion to a variety of surfaces, including other granulocytes, endothelium, and inert substrates. Genetic deficiencies in these molecules result in recurrent bacterial infections due to the inability of granulocytes to mediate an anti-microbial inflammatory response. Patients who are deficient in these molecules are characterized by an elevated leukocyte count (called "leukocytosis") and functional defects in phagocyte activity as measured in vitro by reduced or absence of aggregation adhesion to substrates, chemotaxis, and phagocytosis of opsonized particles. Activation of granulocytes and monocytes by soluble inflammatory mediators increases expression of these molecules (Todd. R.F. III, Arnaout, M.A., Rosin, R.E., Crowley, C.A., Peters, W.A., and Babior, B.M. The subcellular localization of Mol (Mol alpha; formerly gp 110), a surface of glycoprotein associated with neutrophil adhesion, *J. Clin. Invest.*, 74:1280–1290, 1984; Arnaout, M.A., Hakim, R.M. Todd, R.F., Dana, N. and Colten, H.R. Increased expression of an adhesion-promotion surface glycoprotein in the granulocytopenia of hemodialysis. *New Engl. J. Med.,* 312:457–462, 1985). Monoclonal antibodies directed against the Mol glycoprotein effectively prevent neutrophil aggregation in vitro as well as prevent phagocytosis.

The Mol glycoprotein has been of particular interest because its molecular structure has the capacity to bind a component termed "iC3b", a fragment of the third component of complement (Arnaout, M.A., Todd, R.F. III, Dana N., Melamed, J., Schlossman, S.F., and Colten, H.R. Inhibition of phagocytosis of complement C3 or IgG-coated particles and of iC3b binding by monoclonal antibodies to a monocyte-granulocyte membrane glycoprotein (Mol), *J. Clin. Invest.,* 72:171-179, 1983. Also, the Mol glycoprotein is critically important in all of the adhesion-dependent phagocyte functions. Different monoclonal antibodies have been shown to inhibit the functions of the Mol glycoprotein.

The monoclonal antibody derived from the novel hybrid cell line embodying the invention is capable of inhibiting the adhesion-dependent function of, but does not bind the iC3b fragment of the third component of complement. This monoclonal antibody is identified by the designation "MY904". It binds to specific antigenic sites of neutrophils, i.e. to the antigenic site on the CD11b/CD phagocyte surface protein which is specifically involved in granulocyte adhesion. The addition of the MY904 monoclonal antibody to phagocytes will thus inhibit adhesion-dependent phagocyte functions; but it does not inhibit other functions of either the CD11b/CD18 molecule, such as binding of complement component iC3b, or other types of neutrophil or monocyte functions, such as Fc receptor activation, activation of the respiratory burst by chemotactic peptide or phorbol diester and others.

The utility for such a site specific monoclonal antibody is very diversified. The binding of the MYg04 monoclonal antibody to the adhesion dependent domain of neutrophils could specifically inhibit neutrophil migration to an area of inflammation or infection. In addition, such binding to neutrophils could inhibit adhesion and spreading of activated neutrophils already within such an inflammatory or infected site, thus blocking the release of toxic substances by the neutrophils. The monoclonal antibody MY904 could be labelled with a suitable marker for immunoassay of the CD11b/CD18 molecule or be conjugated to a suitable substrate for depletion of bound cells by fluorescence activated cell sorting or magnetic bead separation. The ability of the MY904 monoclonal antibody to block certain phagocyte functions would have special utility for in depth studY of phagocyte function, especially where excess or harmful phagocyte function is involved in clinical disorder. Further, this monoclonal antibody is useful for quantitating surface expression of CD11b/CD18 and thereby can be applied to diagnose the Mol deficiency disease described herein.

SUMMARY OF THE INVENTION

A hybrid cell line which produces a monoclonal antibody specific for the adhesion-dependent domain of the Mol antigen expressed on the surface of human and animal phagocytes. The monoclonal antibody is specific for the part of the Cd11b/CD18 phagocyte cell surface protein involved in adhesion of neutrophils and monocytes, and thus, the monoclonal antibody blocks adhesion-dependent phagocyte functions, such as chemotaxis and phagocytosis to an inflammatory or infection site without affecting certain other phagocyte functions thereof.

The monoclonal antibody is produced by a hybrid cell line in which one of the fusion partners was immunized to human chronic granulocyte leukemia cells.

PREFERRED EMBODIMENT OF THE INVENTION

The monoclonal antibody of the invention is identified by the designation MY904. It was developed from the fusion of mouse spleen cells immunized with purified chronic granulocytic leukemia (CGL) and mouse myeloma cells by a standard procedure described by Kohler and Milstein, *Nature* 256:495-497 (1975).

The human CGL cells used in the immunization procedure were unique and specifically prepared. Blood was obtained by venopuncture from a single patient with CGL in the blast phase for routine diagnostic studies. Mononuclear cells were prepared by Ficoll-Hypaque gradient density sedimentation, 1.077 g/cc. The mononuclear cells were then cryopreserved in 10% dimethylsulfoxide in the vapor phase of liquid nitrogen until used. For immunization, aliquots of the CGL cells were thawed, suspended in phosphate buffered saline (PBS). and $10 \times 10^6$ cells were injected into the peritoneal cavity and subcutaneous areas of a Balb/c mouse. This procedure was repeated at weekly intervals for one (1) month. After an additional period of one (1) month, the mouse was boosted with $10 \times 10^6$ cells from the same patient injected intravenously into a tail vein of the mouse. Three (3) days later, the spleen of the mouse was recovered and the spleen cells harvested by conventional techniques.

The fusion to form hybridomas followed. The spleen cells were washed and mixed with the NS-1 plasmacytoma cell line at a ratio of eight (8) spleen cells to the NS-1 cell in serum-free medium. The cells were centrifuged to pellet form and suspended in 0.5 ml of 30% polyethyleneglycol (PEG) for eight (8) minutes at 25° C. The PEG was decanted, the cells diluted in hypoxanthineaminopterin-thymidine media and distributed to microtiter plates. Tests for reactivity of the monoclonal antibody MY904 were performed by indirect immunofluorescence and flow cytometry, screening being for reactivity with CGL cells from the original patient. The MYg04 monoclonal antibody was selected by virtue of this reactivity with the immunizing CGL cells and lack of reactivity with normal human T lymphocytes and B lymphocytes.

The MY904 monoclonal antibody was shown to react with purified monocytes of 10/10 normal donors tested, 10/10 normal granulocytes tested, and 10/10 samples of normal bone marrow mononuclear cells. It did not react with purified B lymphocytes. Low antigen density was detected on a subset of peripheral blood large granular lymphocytes which had been shown to include the natural killer cells. The cell line KG-1 maintained in tissue culture was tested and shown to be positive for the MY904 epitope. The HL-60 and U937 myeloid cell lines were tested and shown to be negative, but if they are induced to differentiate in vitro by the addition phorbol diester, both CELL lines will then express the MYg04 epitope. The following cell lines were tested and shown to be negative: K562, Daudi, Nalm-1, Nalm-6, JB, Raji, CEM, HSB, and 5 Epstein-Barr-transformed B lymphocyte cell lines (Laz-221, -388, -156, -471, -509). Normal erythrocytes and platelets lack expression of MY904, as do phytohemagglutinin-activated T lymphocytes.

Expression of the MY904 epitope on human leukemic cells was studied. The antibody reacts with granulocytes from all patients with stable phase chronic granulocytic leukemia (CGL). Thirty patients with the blast phase of chronic granulocytic leukemia were studied. The blast cells from 9 cases were positive. One hundred ninety-three cases of acute myeloblastic leukemia were studied; the MY904 monoclonal antibody reacted with leukemic cells of 56% of these patients.

The monoclonal antibody is of the IgG1 subclass and immunopreciptitates of glycoprotein composed of two (2) sub-units of 155,000 daltons and 94,000 daltons molecular weight from surface labelled normal human granulocytes (Dana, N., et al. Two functional domains in the phagocyte membrane glycoprotein Mol identified wit monoclonal antibodies. *J. Immunol.* 137:3259–3263, 1986). The distribution of reactivity of monoclonal antibody MY904 does not inhibit iC3b binding, but it is a potent inhibitor of the adhesion-dependent processes, granulocyte spreading on plastic and chemotaxis. Dana et al., ibid. In comparison with other anti-Mol monoclonal antibodies, the MY904 monoclonal antibody was unique in that it inhibited only adhesion-dependent functions but non binding of iC3b. Other antibodies tested included monoclonal antibodies 44, 903, 94, 17, OKM10, and Leu-15. Dana et al., ibid.

Thus, monoclonal antibody MY904 identifies the Mol granulocyte/monocyte cell surface glycoprotein, and further binds specifically to an epitope on that glycoprotein which is involved in adhesion-dependent processes of granulocyte/monocyte activities.

A sample of the hybrid cell line capable of producing MY904 monoclonal antibodies is on deposit with the American Type Culture Collection, (A.T.C.C.) 12301 Parklawn Drive, Rockville, MD 20852, as of Aug. 19, 1988 and is assigned A.T.C.C. No. HB 9510.

Studies in vitro have shown that human, canine and sub-human primate leukocytes have in common the Mol glycoprotein. Letvin, N.L., Todd, R.F. III, Palley, L.S., and Griffin, J.D. Conservation of the MY904 myeloid surface antigen on primate and canine granulocytes has been demonstrated (*Blood* 61:408–410, 1983). Also, binding of the MY904 monoclonal antibody to normal dog neutrophils has been shown to effectively inhibit neutrophil aggregation in vitro when stimulated with the phorbol ester PMA (Giger, U., Boxer, L.A., Simpson, P.A., Lucchesi, B.R., and Todd, R.F. III. Deficiency of leukocyte surface glycoproteins Mol, LFA-1, and Leu-M5 in a dog with recurrent bacterial infection: an animal model. *Blood* 69: 1622–1630, 1987).

The MY904 monoclonal antibody is unique because of its exceptional specificity for the adhesion domain of the CD11b/CD18 phagocyte surface protein. Further, this antibody has the ability to completely inhibit phagocyte functions which require expression of this critical cell surface structure.

We claim:

1. A monoclonal antibody which binds specifically to the epitope defined by the MY904 antibody, wherein said binding inhibits only the adhesion-dependent functions of granulocytes and monocytes without binding the iC3b component of complement, and wherein the antibody does not bind human T and B lymphocytes, said MY904 antibody being the antibody produced by the hybridoma having ATCC accession number HB9510.

2. A hybridoma cell line which produces the antibody of claim 1.

3. The cell line of claim 2 wherein said monoclonal antibody binds specifically to granulocytes from peripheral blood samples of chronic granulocytic leukemia origin.

4. The cell line of claim 2 wherein the monoclonal antibody binds specifically to normal monocytes, normal granulocytes and normal bone marrow mononuclear cells and does not bind to normal erthrocytes and platelets.

5. The cell line produced by a hydridoma technique having all the identifying characteristics of the sample on deposit with the American Type Culture Collection No. HB9510 producing monoclonal antibody MY904 that specifically binds to the adhesion-domain of the CD116/CD18 phagocyte surface protein.

6. The monoclonal antibody of claim 1 which binds specifically to normal monocytes, normal granulocytes and normal bone marrow mononuclear cells and does not bind to normal erythrocytes and platelets.

7. The monoclonal antibody of claim 1 which does not bind specifically to normal erythrocytes and platelets.

8. The monoclonal antibody of claim 1 produced by the hybrid cell line having all the identifying characteristics of the A.T.C.C. deposit No. HB 9510.

9. The monoclonal antibody of claim 1 which does not bind specifically to human T or B lymphocytes.

* * * * *

UNITED STATES PATENT AND TRADEMARK OFFICE
CERTIFICATE OF CORRECTION

PATENT NO. : 5,019,648

DATED : May 28, 1991

INVENTOR(S) : Stuart F. Schlossman and James D. Griffin

It is certified that error appears in the above-identified patent and that said Letters Patent is hereby corrected as shown below:

Column 1, line 51, after "marrow" insert a --comma (,)--.

Column 3, line 13, after "function of" insert --neutrophils--.

Column 3, line 30, correct "MYg04" to --MY904--.

Column 3, line 46, correct "studY" to --study--.

Column 4, line 41, correct "MYg04" to --MY904--.

Column 4, line 56, after "addition" insert --of--.

Column 4, line 57, change "CELL" to --cell--.

Column 4, line 58, correct "MYg04" to --MY904--.

Column 5, line 7, change "of" (first occurrence) to --a--.

Column 5, line 32, change "1988" to --1987--.

UNITED STATES PATENT AND TRADEMARK OFFICE
CERTIFICATE OF CORRECTION

PATENT NO. : 5,019,648

DATED : May 28, 1991

INVENTOR(S) : Stuart F. Schlossman and James D. Griffin

It is certified that error appears in the above-identified patent and that said Letters Patent is hereby corrected as shown below:

Column 6, line 33, correct "CD116/CD18" to --CD11b/CD18--.

Signed and Sealed this

Twenty-sixth Day of November, 1991

*Attest:*

HARRY F. MANBECK, JR.

*Attesting Officer*      *Commissioner of Patents and Trademarks*